US 6,551,993 B1

(12) United States Patent
Schneider

(10) Patent No.: US 6,551,993 B1
(45) Date of Patent: Apr. 22, 2003

(54) PARTIAL AGONISTS AT THE GLYCINE MODULATORY SITE OF THE NMDA RECEPTOR FOR TREATING COGNITIVE DYSFUNCTION

(75) Inventor: Jay S. Schneider, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/639,611

(22) Filed: Aug. 15, 2000

Related U.S. Application Data
(60) Provisional application No. 60/149,082, filed on Aug. 16, 1999.

(51) Int. Cl.$^7$ .......................... A61K 31/41; A61K 31/42
(52) U.S. Cl. ............................. 514/8; 514/12; 514/359; 514/380; 514/561
(58) Field of Search ............................. 514/8, 12, 359, 514/380, 561

(56) References Cited

U.S. PATENT DOCUMENTS

| | | | | |
|---|---|---|---|---|
| 5,187,171 A | * | 2/1993 | Cordi | ........................ 514/359 |
| 5,468,763 A | * | 11/1995 | Cordi et al. | ................. 514/380 |
| 6,162,827 A | * | 12/2000 | Javitt | ........................ 514/561 |

OTHER PUBLICATIONS

Lippincott's Illustrated Reviews, Pharmacology, Second Edition, Chapter 8, "Treatment of Parkinson's Disease" (1997).*
Aigner, T.G., "Pharmacology of memory: cholinergic–glutamatergic interactions," *Curr. Opin. Neurobiol.*, 1995, 5, 155–160.
Albin, R.L., et al., "The functional anatomy of basal ganglia disorders," *Trends Neurosci*, 1989, 12, 366–375.
Bischoff, C., et al., "Competitive and non–competitive NMDA receptor antagonists in spatial learning tasks," *Eur. J. Pharmacol.*, 1992, 213, 269–273.
Brotchie, J.M., et al., "Alleviation of parkinsonism by antagonism of excitatory amino acid transmission in the medial segment of the *globus pallidus* in rat and primate," *Nov. Disord.*, 1991, 6, 133–138.
Collingridge, G.L., et al., "NMDA receptors–their role in long–term potentiation," *Trends Neurosci.*, 1987, 10, 288–293.
Crossman, A.R., et al., "Atagonist MK–801 on MPTP–induced parkinsonism in the monkey," *Neuropharmacol,* 1989, 11, 1271–1273.
Domino, E.F., et al., N–methyl–D–aspartate receptor antagonist and dopamine D1 and D2 agonist interactions in 1–methyl–4–phenyl–1,2,5,6–tetrahydropyridine–induced hemiparkinsonian monkeys, *J. Pharmacol. Exp. Ther.*, 1993, 264, 221–225.

Fishkin, R.J., et al., "D–cycloserine attenuates scopolamine–induced learning and memory deficits in rats," *Behav. Neural. Biol.*, 1993, 59, 150–157.
Gozlan, H., et al., "NMDA receptor redox sites: are they targets for selective neuronal protection?," *TIPS,* Nov. 1995, 16, 368–374.
Greenamyre, J.T., et al., "Antiparkinson effects of remacemide hydrochloride, a glutamate antagonist, in rodent and primate models of Parkinson's disease," *Ann. Neurol.,* 1994, 35, 655–661.
Klockgether, T., et al., "Antagonists potentiate antiparkinsonian actions of L–dopa in nonoamine–depleted rats," *Ann. Neurol.,* 1990, 28, 539–546.
Klockgether, T., et al., "The AMPA receptor antagonist NBQX has antiparkinsonian effects in monoamine depleted rats and MPTP treated monkeys," *Ann. Neurol.,* 1991, 30, 717–723.
Lanthorn, T.H., "d–Cycloserine: agonist turned antagonist," *Amino Acids,* 1994, 6, 247–260.
Lipton, S.A., et al., "Excitatory amino acids as a final common pathway for neurologic disorders," *Mechanisms of Disease,* Mar. 3, 1994, 330(9), 613–622.
Matsuoka, N., et al., "Cholinergic–glutamatergic interactions in visual recognition memory of rhesus monkeys," *NeuroReport,* 1996c, 7, 565–568.
Matsuoka N., et al., "The glycine/NMDA receptor antagonist HA–966 impairs visual recognition memory in rhesus monkeys," *Brain Res.,* 1996, 731, 72–78.
Matsuoka N., et al., D–cylsoserine, a partial agonist at the glycine site coupled to N–methyl–D–aspartate receptors, improves visual recognition memory in rhesus monkeys, *J. Pharmacol. Exp. Ther.,* 1996a, 278, 891–897.
Menzaghi, F., et al., "Characterization of SIB–1508Y, the active enantiomer of a novel nicotinic acetylcholine receptor (NaChR) agonist, SIB–1765F," *Soc. Neurosci Abstr.,* 1996, 22, 1523.
Nishimura, L.M., et al., "N–methyl–D–aspartate–evoked release of acetylcholine form the medial septum/diagonal band of rat brain," *Neurosci Lett.,* 1990, 115, 259–264.
Ogura H., et al., "Impairs recognition memory in rhesus monkeys: comparison with cholinergic drugs," *J. Pharmacol. Exp. Ther.,* 1993, 266, 60–64.
Ohno, M., et al., "Intrahippocampal administration of a glycine site antagonist impairs working memory performance of rats," *Eur. J. Pharmacol.,* 1994, 253, 183–187.
Ramsom, R.W., et al., "Glycine modulation of NMDA–evoked release of [3H]acetylcholine and [3H]dopamine from rat striatal slices," *Neurosci Lett.,* 1989, 96, 323–328.

(List continued on next page.)

Primary Examiner—Frederick Krass
(74) Attorney, Agent, or Firm—Drinker Biddle & Reath LLP

(57) ABSTRACT

The present invention involves the use of partial glycine agonists directed at the glycine modulatory site of the NMDA receptor to treat cognitive dysfunction in mammals with Parkinson's disease or schizophrenia.

7 Claims, 2 Drawing Sheets

OTHER PUBLICATIONS

Rupniak, N.M.J., et al., "Induced by combined treatment with L–dopa and MK–801 in parkinsonian monkeys," *Ann. Neurol.,* 1992, 32, 103–105.

Rupniak, N.M.J., et al., "Failure of D–cycloserine to reverse cognitive disruption induced by scopolamine or phencyclidine in primates," *Life Sci.,* 1992, 50, 1959–1962.

Sacaan, A.I., et al., "Dopamine (DA) and norepinephrine (NE) release in the prefrontal cortex (PFC) are regulated by different nAChR subtypes," *Soc. Neurosci Abstr.,* 1997, 23, 1200.

Schmidt, W.J., et al., "Anticataleptic effects of the N–methyl–D–asparate antagonist MK–801 in rats," *Pharmacol. Biochem. Behav.,* 1989, 32, 621–623.

Schneider, J.S., et al., "Nicotinic acetylcholine receptor agonist SIB–1508Y improves cognitive functioning in chronic low dose MPTP–treated monkeys," *J. Pharmacol. Exp. Ther.,* 1999, 290(2), 731–739.

Schneider, J.S., et al., "Effects of the nicotinic acetylcholine receptor agonist SIB–1508Y on object retrieval performance in MPTP–Treatment monkeys: comparison with levodopa treatment," *Ann Neurol. Assoc.,* 1998, 43, 311–317.

Schneider, J.S., et al., "Delayed matching–to–sample, object retrieval, and discrimination reversal deficits in chronic low dose MPTP–treated monkeys," *Brain Res.,* 1993, 615, 351–354.

Schneider, J.S., "Chronic exposure to low doeses of MPTP. II. Neurochemical and pathological consequences in cognitively–impaired, motor asymptomatic monkeys," *Brain Res.,* 1990, 534, 25–36.

Schneider, J.S., et al., "Chronic exposure to low doses of MPTP. I. Cognitive deficits in motor asymptomatic monkeys," *Brain Res.,* 1990, 519, 122–128.

Sirvio, J., et al., "A modulator of the N–methyl–D–aspartate receptor, improves spatial learning in rats treated with muscarinic antagonist," *Neurosci. Lett.,* 1992, 146, 215–218.

Watson, G.B., et al., "D–cycloserine acts as a partial agonist at the glycine modulatory site of the NMDA receptor expressed Xenopus oocytes," *Brain Res.,* 1990, 510, 158–160.

* cited by examiner

PARTIAL AGONISTS AT THE GLYCINE MODULATORY SITE OF THE NMDA RECEPTOR FOR TREATING COGNITIVE DYSFUNCTION

This application claims the benefit of U.S. Provisional Application No. 60/149,082, filed Aug. 16, 1999.

GOVERNMENT RIGHTS IN THE INVENTION

This invention was made with government support under grant MH 46531 awarded by the National Institutes of Health. The government has certain rights in the invention.

FIELD OF THE INVENTION

The present invention generally relates to the field of neurology and neuropharmacology and, more particularly, to the use of partial agonists at the glycine modulatory site of the NMDA receptor to treat cognitive dysfunction in Parkinson's disease and in schizophrenia.

BACKGROUND OF THE INVENTION

The potential role of glutamatergic drugs in the treatment of Parkinson's disease (PD) has received considerable interest in the last several years. The popular theory of basal ganglia circuitry proposes that basal ganglia output neurons in the internal segment of the globus pallidus (GPi) and the substantia nigra pars reticulata (SNr) are regulated in part by glutamatergic inputs from the subthalamic nucleus. (Albin R L, Young A B, Penny J B. The functional anatomy of basal ganglia disorders. *Trends Neurosci* 12:366–375, 1989). Overactivity of these subthalamic glutamatergic projections are believed to result in excessive inhibition of thalamic neurons that receive GPi and SNr inputs and underlies expression of parkinsonian motor signs. (Albin et al., 1989). Based on this, it has been suggested that treatment with glutamate antagonist drugs might have beneficial anti-Parkinson actions. (Greenamyre J T, Eller R V, Zhang Z, Ovadia A, Kurlan R, Gash D M. Antiparkinson effects of remacemide hydrochloride, a glutamate antagonist, in rodent and primate models of Parkinson's disease. *Ann Neurol* 35:655–661, 1994). Indeed, the non-competitive NMDA antagonist MK-801 has been shown to increase locomotion in dopamine-depleted rats (Klockgether T, Turski L. NMDA antagonists potentiate antiparkinsonian actions of L-dopa in monoamine-depleted rats. *Ann Neurol* 28:539–546, 1990) and reverse neuroleptic-induced catalepsy in rats (Schmidt W J, Bubser M. Anticataleptic effects of the N-methyl-D-aspartate antagonist MK-801 in rats. *Pharmacol Biochem Behav* 32:621–623, 1989). In addition, stereotaxic administration of glutamate antagonists into the GPi or SNr ameliorated parkinsonian features in 1-methyl, 4-phenyl, 1,2,3,6-tetrahydropyridine (MPTP)-treated monkeys. (Brotchie J M, Mitchell U, Sambrook M A, Crossman A R. Alleviation of parkinsonism by antagonism of excitatory amino acid transmission in the medial segment of the globus pallidus in rat and primate. *Mov Disord* 6:133–138, 1991; Klockgether T, Turski L, Honore T, Zhang Z M, Gash D M, Kurlan R, Greenamyre J T. The AMPA receptor antagonist NBQX has antiparkinsonian effects in monoamine depleted rats and MPTP treated monkeys. *Ann Neurol* 30:717–723, 1991).

However, several studies utilizing systemically administered NMDA antagonists to parkinsonian monkeys have not had the predicted anti-Parkinson effect. Many studies have shown that administration of MK-801 to parkinsonian monkeys either has no effect or exacerbates the parkinsonian features (Crosssman A R, Peggs D, Boyce S, Luquin M R, Sambrook M A. Effect of the NMDA atagonist MK-801 on MPTP-induced parkinsonism in the monkey. *Neuropharmacol* 11:1271–1273, 1989; Rupniak N M J, Duchnowski M, Tye S J, Cook G, Iversen S D. Failure of D-cycloserine to reverse cognitive disruption induced by scopolamine or phencyclidine in primates. *Life Sci* 50:1959–1962, 1992). Additionally, while some studies claim that glutamate antagonists potentiate levodopa responses in parkinsonian monkeys (Greenamyre et al., 1994), others have shown antagonistic effects on levodopa and dopamine agonist-induced functional improvements. (Crosssman et al., 1989; Rupniak N M J, Boyce S, Steventon M J, Iversen S D, Marsden CD. Dystonia induced by combined treatment with L-dopa and MK-801 in parkinsonian monkeys. *Ann Neurol* 32:103–105, 1992; Domino E F, Sheng J. N-methyl-D-aspartate receptor antagonist and dopamine D1 and D2 agonist interactions in 1-methyl-4-phenyl-1,2,5,6-tetrahydropyridine-induced hemiparkinsonian monkeys. *J Pharmacol Exp Ther* 264:221–225, 1993).

Although it is still unclear as to the therapeutic usefulness of NMDA antagonists in treating the motor dysfunctions of PD, there may be a role for stimulation of the NMDA receptor in treating some of the cognitive sequelae of PD. Several reports have suggested that positive modulation of the NMDA receptor might be useful for the treatment of various learning and memory impairments. Activation of the NMDA receptor leads to long-term potentiation (a mechanism of synaptic modification related to memory formation and learning) (Collingridge G L, Bliss T V P (1987) NMDA receptors-their role in long-term potentiation. *Trends Neurosci* 10:288–293, 1987) and antagonism of NMDA receptors results in disruption of learning and memory processes. (Bischoff C, Tiedtke P I. Competitive and non-competitive NMDA receptor antagonists in spatial learning tasks. *Eur J Pharmacol* 213:269–273, 1992; Ogura H, Aigner T G. MK-801 impairs recognition memory in rhesus monkeys: comparison with cholinergic drugs. *J Pharmacol Exp Ther* 266:60–64, 1993). While potentiating glutamatergic neurotransmission at the NMDA receptor might improve certain cognitive functions, it may also lead to exctitoxicity and cell death.

In the present invention, use of a partial agonist at the glycine modulatory site of the NMDA receptor can circumvent the problem of excitotoxicity while allowing NMDA receptor activation. The glycine-B site on the NMDA receptor is a modulatory site wherein glycine, in the presence of glutamate, acts synergistically with glutamate to promote channel opening and excitatory neurotransmission. One such partial glycine agonist is the antibiotic D-cycloserine. Other such partial glycine agonists include D-serine and serine racemase, the enzyme that converts L-serine to D-serine, thereby promoting endogenous biosynthesis of a partial glycine agonist.

As a partial agonist, D-cycloserine, at low concentrations, acts as an agonist mimicking glycine's effects and stimulating NMDA receptors. (Watson G B, Bolanowski M A, Baganoff M P, Deppeler C L, Lanthorn T H. D-cycloserine acts as a partial agonist at the glycine modulatory site of the NMDA receptor expressed *Xenopus oocytes*. *Brain Res* 510:158–160, 1990; Lanthorn T H. d-Cycloserine: agonist turned antagonist. *Amino Acids* 6:247–260, 1994). At high concentrations, it can antagonize the effects of endogenous glycine, blocking excess stimulation. The present invention demonstrates activation of the glycine/NMDA receptor complex by D-cycloserine to improve cognitive deficits, including those present in Parkinson's disease and in schizophrenia. As noted above, D-serine and serine racemase may also be used in the present invention.

The present invention also involves the combination of D-serine and/or other partial glycine agonists with existing anti-Parkinsonian treatments (such as levodopa/carbidopa and dopamine agonists) to treat Parkinson's disease. While existing treatments enhance motor functioning in Parkinson's patients, they do little to enhance cognitive functioning and, in fact, may worsen cognitive functioning. By combining the partial glycine agonists with existing anti-Parkinsonian treatments, motor and cognitive function in Parkinson's patients can be enhanced, thereby providing a better overall therapeutic effect than with either compound alone.

Definitions

"Partial glycine agonist" means D-serine, serine racemase, D-cycloserine, or another compound that can act functionally like or mimic the action of a partial glycine agonist.

SUMMARY OF THE INVENTION

Accordingly, it is an object of the present invention to provide a method of treating cognitive dysfunction in a mammal having Parkinson's disease, comprising administering a therapeutically effective amount of a partial glycine agonist to the glycine modulatory site of the NMDA receptor lex of said mammal.

It is a further object of the present invention to provide a method of treating cognitive dysfunction in a mammal having Parkinson's disease, comprising administering a therapeutically effective amount of a partial glycine agonist to the glycine modulatory site of the NMDA receptor complex of said mammal, wherein said partial glycine agonist is at least one of the group of D-cycloserine, D-serine, and serine racemase.

It is another object of the present invention to provide a method of treating cognitive dysfunction in a mammal having schizophrenia, comprising administering a therapeutically effective amount of a partial glycine agonist to the glycine modulatory site of the NMDA receptor complex of said mammal.

It is a further object of the present invention to provide a method of treating cognitive dysfunction in a mammal having schizophrenia, comprising administering a therapeutically effective amount of a partial glycine agonist to the glycine modulatory site of the NMDA receptor complex of said mammal, wherein said partial glycine agonist is at least one of the group of D-cycloserine, D-serine, and serine racemase.

It is another object of the present invention to provide a method of treating cognitive dysfunction and motor dysfunction in a mammal having Parkinson's disease, comprising administering a therapeutically effective amount of a partial glycine agonist to the glycine modulatory site of the NMDA receptor complex of said mammal in combination with at least one of the group of levodopa/carbidopa and a dopamine agonist.

It is a further object of the present invention to provide a method of treating cognitive dysfunction and motor dysfunction in a mammal having Parkinson's disease, comprising administering a therapeutically effective amount of a partial glycine agonist to the glycine modulatory site of the NMDA receptor complex of said mammal in combination with at least one of the group of levodopa/carbidopa and a dopamine agonist, wherein said partial glycine agonist is at least one of the group of D-cycloserine, D-serine, and serine racemase.

DETAILED DESCRIPTION

Materials and Methods

Figure 1A:
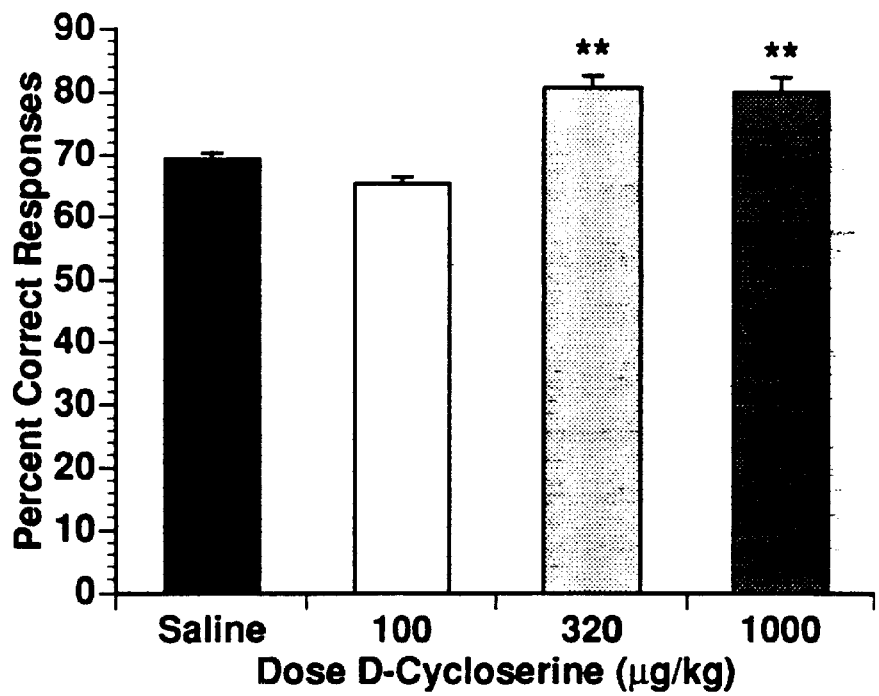
FIG. 1. Effect of D-cycloserine on delayed response FIG. 1(A) and variable delayed response FIG. 1(B) performance in chronic low dose MPTP-treated monkeys. A: Dose response data from D-cycloserine testing (100 to 1000 $\mu$g/kg, i.m.), performed approximately 30 min. after drug administration to monkeys with MPTP-induced cognitive deficits. Data (means±SEM) are combined from 4 animals tested. Baseline (saline) data were derived from testing sessions performed on days prior to and after drug testing. MPTP exposure caused a significant performance deficit (saline) that was at least partially corrected by D-cycloserine. B: Best dose responses (i.e., the most facilitating dose of D-cycloserine for each animal) to D-cycloserine and corresponding noncig baseline responses (saline) on the variable delay response task. Data (means±SEM) are combined from 4 animals tested. Chronic low dose MPTP-exposed monkeys performed poorly at all delays. D-cycloserine administration significantly improved performance at all but the longest delay. Black bars= performance following saline administration; lightly shaded bars=best dose response to D-cycloserine administration. *$p<0.05$ vs. corresponding saline control performance; **$p<0.01$ vs. corresponding saline control performance.

It has been reported previously that monkeys administered low levels of the neurotoxin 1-methy-4-phenyl-1,2,3, 6-tetrahydropyridine (MPTP) exhibit a variety of cognitive deficits reminiscent of the cognitive disturbances noted in PD patients (Schneider J S, Kovelowski C J. Chronic exposure to low doses of MPTP. I. Cognitive deficits in motor asymptomatic monkeys. *Brain Res* 519: 122–128, 1990; Schneider J S, Roeltgen D P. Delayed matching-to-sample, object retrieval, and discrimination reversal deficits in chronic low dose MPTP-treated monkeys. *Brain Res* 615: 351–354, 1993). In addition, Matsuoka and Aigner (Matsuoka N, Aigner T G. D-cylsoserine, a partial agonist at the glycine site coupled to N-methyl-D-aspartate receptors, improves visual recognition memory in rhesus monkeys. *J Pharmacol Exp Ther* 278:891–197, 1996a; Matsuoka N, Aigner T G. The glycine/NMDA receptor antagonist HA-966 impairs visual recognition memory in rhesus monkeys. *Brain Res* 1996) have shown an important role for NMDA channels in cognitive functioning in monkeys and particularly in visual recognition memory. Therefore, the present invention demonstrates activation of the glycine/ NMDA receptor complex by D-cycloserine to improve cognitive deficits in low dose MPTP-treated monkeys.

Subjects

Four adult male cynomolgus monkeys (*Macaca fascicularis*) weighing 5.0–8.0 kg at the beginning of testing were used. All animals had prior behavioral testing experience and had stable cognitive deficits as a result of prior MPTP administration. These animals had previously been used in other pharmacological studies (Schneider J S, Tinker J P, Van Velson M, Menzaghi F, Lloyd G K. Nicotinic acetylcholine receptor agonist SIB-1508Y improves cognitive functioning in chronic low dose MPTP-treated monkeys. *J Pharmacol Exp Ther* 290: In Press, 1999) but had received no drug treatments for at least 6 mos. prior to the start of this study. This study was approved by the Institutional Animal Care and Use Committee at Thomas Jefferson University and performed in accordance with the NIH Guide for the Care and Use of Laboratory Animals.

Behavioral Procedures

Three of the four animals were tested in a modified Wisconsin General Test Apparatus (WGTA) (Schneider and Kovelowski, 1990); one animal performed computer automated tasks while seated in front of a touch sensitive computer monitor located in a darkened sound-attenuated cubicle. All monkeys performed a spatial delayed response (DR) task, a variable delayed response task (VDR) and a visual discrimination (VD) task.

The monkeys that performed in the WGTA sat in a restraining chair situated in a sound-attenuating chamber with background masking noise, behind an opaque screen that when raised, allowed access to a sliding tray. The tray contained recessed food wells and identical sliding red Plexiglas covers that served as stimulus plaques that could be displaced by the animal to obtain rewards (raisins, dried fruit, marshmallows). The monkeys were trained to retrieve food from one of the wells after observing the experimenter bait a well. Right and left wells were baited in a balanced order. Each daily session consisted of 30 trials. For VDR testing, five different delay lengths (2, 5, 10, 20 and 30 secs.) were randomly distributed in blocks of trials over the 40 trials that made up a daily testing session. For VD testing, monkeys were trained to discriminate between two patterns (a cross and a horizontal bar) on otherwise identical Plexiglas covers. The position of the positive stimulus (cross) over the left or right food well varied pseudorandomly. The cover had to be displaced in order to retrieve reward from the recessed food well beneath the cover. A test session consisted of 30 trials. Animals were food deprived overnight prior to testing the next day.

The monkey that performed the computer automated tasks sat in a restraining chair situated in a sound-attenuating chamber with background masking noise, and faced a touch sensitive computer screen with a lever located beneath it. The animal initiated a DR or VDR trial by holding down the lever for one to three seconds. This caused the cue, a filled white circle one inch in diameter, to appear on the right or left side of the screen for two seconds. The cue was then extinguished for a delay period (five seconds for DR; 2, 5, 10, 20, and 30 secs. for VDR) and then identical left and right choice stimuli (filled red circles, one inch in diameter) were presented. The monkey was rewarded with a fruit flavored drink from an automatic dispenser if it touched the response light located on the same side as where the cue appeared. Side of cue presentation was counter-balanced and left/right rewards were distributed pseudorandomly over the 30 trials (40 trials for VDR) that made up a daily testing session. This animal was tested in the morning and fluid deprived overnight prior to testing.

The monkey performed the VD task using the same apparatus described above. The monkey was presented with two shapes on the computer screen: a cross and a horizontal bar, one presented on the right side of the screen and the other presented on the left side of the screen. The monkey was trained to respond to (i.e., touch) the cross, regardless of position on the screen, to obtain juice reward. Each test session consisted of 30 trials.

Drug Testing

Animals initially received low doses of MPTP for periods of up to 178 days until stable cognitive deficits (consistent performance deficits of at least 15% on DR) were observed (Schneider et al., 1999). These animals had not received any MPTP for at least 9 months prior to the start of this study. Drug effects were determined for D-cycloserine and MK-801 (Research Biochemicals International, Natick, M A) at doses of 100, 320, 1,000, and 8,000 $\mu$g/kg and 10, 20 or 32 $\mu$g/kg, respectively. Drugs were dissolved in sterile physiological saline just prior to use and administered by intramuscular injection approximately 30 min. prior to the start of the test session. Each dose was tested twice and doses were administered in random order. Control sessions were performed following injection of saline vehicle. Saline control sessions were performed on days before and after each drug session. Drugs were administered no more than twice per week, with at least 2–3 days and a saline control session between drug test sessions.

Data Analysis

All data were expressed as mean±S.E.M. Task performance on drug was compared with matched control (saline) performance. Animals served as their own controls and thus statistical analyses of the results from different doses of D-cycloserine or MK-801 employed a repeated measures one way analysis of variance (ANOVA) followed by pairwise post hoc comparisons (Dunnett's multiple comparison test, two-tailed) of saline and drug performances.

Results

As reported previously (Schneider et al., 1999), the animals used in this study, similar to other chronic low dose MPTP-treated monkeys (Schneider and Kovelowski, 1990), developed stable deficits in DR and VDR performance but continued to perform the VD task almost flawlessly. Also as previously reported (Schneider et al., 1999) animals learned the automated and non-automated tasks to similar criterion levels and the tasks were disrupted to a similar degree by MPTP exposure and responded similarly to drug treatments. This suggested that although technically different, the tasks were assessing the same cognitive domains. Thus, the data from automated and non-automated testing were combined for analysis.

D-cycloserine treatment caused dose dependent improvements in both DR and VDR performance. In the DR task, D-cycloserine treatment significantly altered task performance ($F(3,73)=11.26$, $p<0.0001$) with doses of 320 ($t=6.73$, $p<0.01$) and 1,000 $\mu$g/kg ($t=3.76$, $p<0.05$) significantly improving task performance when compared to saline (FIG. 1A). Neither the low (100 $\mu$g/kg) nor high (8,000 $\mu$g/kg) doses of D-cycloserine had any effect on DR performance.

Figure 1B:
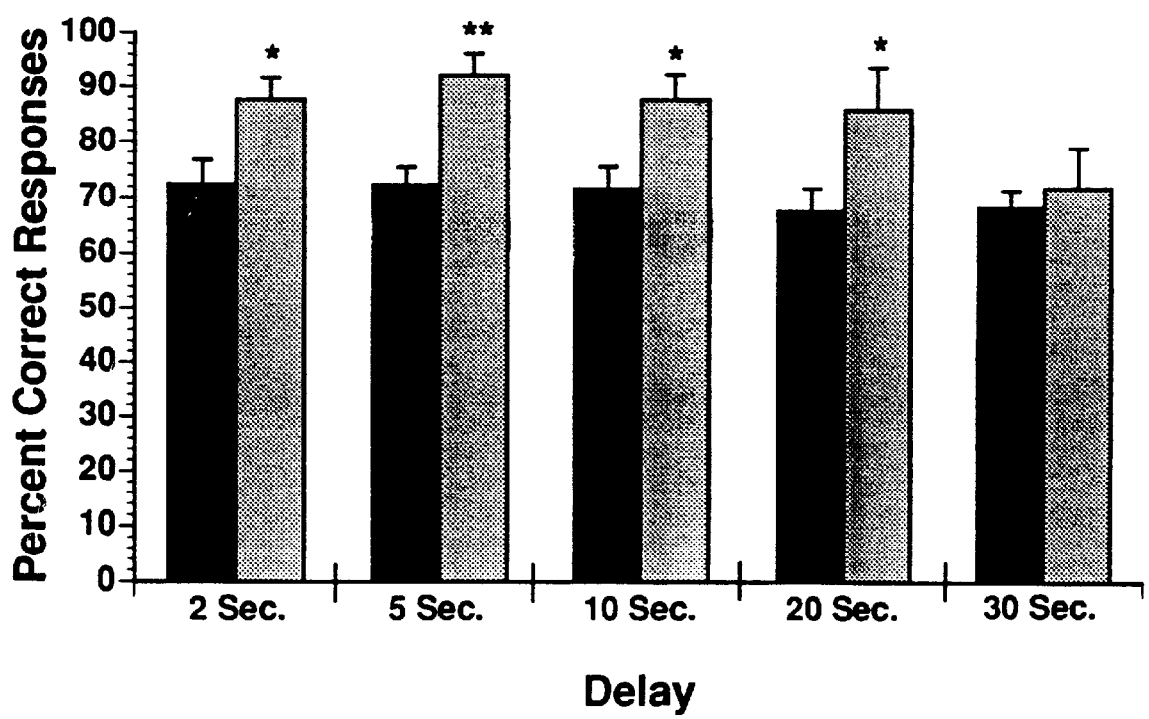

Delay analysis revealed no significant effect of delay ($F(4,85)=0.41$, $p=0.80$) on VDR performance in the MPTP-treated animals. However, there was a significant interaction of D-cycloserine treatment and delay ($F (14,109)=5.13$, $p<0.0001$). At all delays, the 100 $\mu$g/kg dose of D-cycloserine had no effects on ask performance. The 320 $\mu$g/kg dose significantly improved performance at 2, 5, and 20 sec. delays while the 1,000 $\mu$g/kg dose significantly improved performance at 2, 5, and 10 sec delays. None of the doses of D-cycloserine improved performance at the 30 sec. delay. The effects of the best (most efficacious) dose of D-cycloserine vs. saline control performance at the different delay lengths are shown in FIG. 1B.

Figure 2:
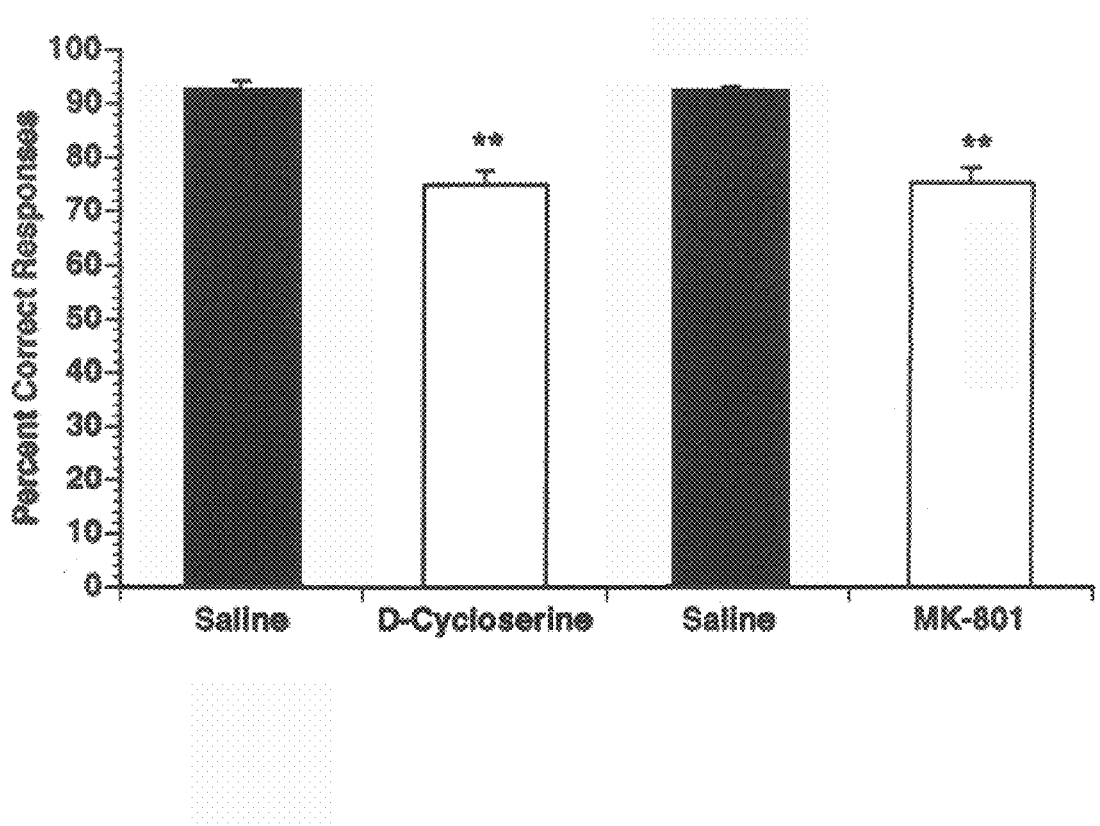
FIG. 2. Effect of high dose D-cycloserine and the NMDA antagonist MK-801 on visual discrimination performance in chronic low dose MPTP-treated monkeys. Visual discrimination performance was not disrupted by MPTP exposure as evidenced by over 90% correct performance on saline control trials. In contrast, visual discrimination performance was significantly disrupted by high dose D-cycloserine (8,000 $\mu$g/kg) and by MK-801 administration (10–32 $\mu$g/kg) at doses that did not significantly impair motor functioning. **$p<0.01$ vs. saline control performance.

D-cycloserine treatment (100 to 1,000 $\mu$g/kg) had no effects on VD performance which was not impaired by MPTP exposure (Schneider and Kovelowski, 1990; Schneider et al., 1999). However, a large dose of D-cycloserine (8,000 μg/kg) significantly impaired VD performance in all animals (FIG. 2), while causing neither improvement nor further disruption of DR or VDR performance. The NMDA receptor blocker MK-801 (10–32 μg/kg) also had no effects on DR performance but caused a significant impairment in VD performance in all animals (FIG. 2).

Discussion

The results of this study show that D-cycloserine, a partial agonist at the glycine recognition site on the NMDA receptor complex, can significantly improve the MPTP-induced spatial short-term memory deficit in chronic low dose MPTP-treated monkeys. Since D-cycloserine improved performance at both short (2 sec.) and long (20 sec.) delays, this drug may have effects on both attention as well as memory components of task performance. While a previous study showed that D-cycloserine could modulate cognitive function and significantly improve visual recognition memory in normal monkeys (Matsuoka and Aigner, 1996a), this is the first study to demonstrate that D-cycloserine can improve cognitive functioning in monkeys with altered brain neurochemistry, in this case induced by chronic MPTP administration. Although data from non-human primates is lacking, previous studies in rodents have shown enhanced memory (Sirvio J, Ekonsalo T, Riekkinen P, Lahtinen, H, Riekkinen P. D-cycloserine, a modulator of the N-methyl-D-aspartate receptor, improves spatial learning in rats treated with muscarinic antagonist. *Neurosci Lett* 146:215–218, 1992; Fishkin R J, Ince E S, Carlezon, W A, Jr, Dunn R W. D-cycloserine attenuates scopolamine-induced learning and memory deficits in rats. *Behav neural Biol* 59:150–157, 1993) and antagonism of scopolamine and lesion-induced memory deficits with D-cycloserine and have even emphasized the importance of glycine receptors in short-term or working memory. (Ohno M, Yamamoto T, Watanabe S. Intrahippocampal administration of a glycine site antagonist impairs working memory performance of rats. *Eur J Pharmacol* 253:183–187, 1994).

Glycine influences the activity of glutamate at the NMDA receptor and both glutamate and glycine bending are required for activation of the NMDA receptor-associated cation channel. As a partial agonist at the glycine modulatory site of the NMDA receptor, D-cycloserine can either augment or antagonize the effect of glycine depending upon endogenous glycine concentrations (Watson et al., 1990). Thus, D-cycloserine effects on the NMDA receptor complex should be stimulatory when endogenous glycine concentrations are low and antagonistic in the presence of glycine excess. Assuming that the NMDA receptor complex is not saturated by endogenous ligand, D-cycloserine may enhance function of cells without causing potentially detrimental overstimulation as may occur with use of an NMDA agonist.

The neurochemical deficits underlying the cognitive dysfunctions in chronic MPTP-treated monkeys are complex and not completely understood. Chronic low dose MPTP administration resulted in decreased cortical norepinephrine levels although cortical dopamine levels were relatively intact in many regions sampled (Schneider J S. Chronic exposure to low doses of MPTP. II. Neurochemical and pathological consequences in cognitively-impaired, motor asymptomatic monkeys. *Brain Res* 534: 25–36, 1990). Both dopamine and norepinephrine levels were decreased in the striatum, with the most significant decreases in the caudate nucleus (Schneider, 1990). Since the greatest deficit was in striatal dopamine levels in these animals, we suggested that this striatal dopaminergic deficit might underlie the cognitive disturbances in these animals although decreased norepinephrine levels in the frontal cortex and striatum were also likely contributing factors to the attentional and memory problems observed in these monkeys (Schneider, 1990). Yet, recent pharmacological studies have shown that dopamine replacement therapy (levodopa) was ineffective in substantially reversing the cognitive deficits in these animals while treatment with neuronal nicotinic acetylcholine receptor (nAChR) agonists significantly improved performance on a variety of cognitive tasks (Schneider J S, Van Velson M, Menzaghi F, Lloyd, G K. Treatment with the nicotinic acetylcholine receptor agonist SIB-1508Y improves object retrieval performance in MPTP-treated monkeys: Comparison with levodopa treatment. *Ann Neurol* 43: 311–317, 1998; Schneider et al., 1999). The cognitive deficits in chronic low dose MPTP-treated monkeys and most likely in Parkinson's disease patients most likely arise from dysfunction of several cortical and subcortical neurotransmitter systems and functional circuits, such that L-dopa treatment alone cannot sufficiently normalize behavior. The superior effects of nAChR agonists may be due to the ability of these drugs to release dopamine from striatal, limbic and frontal cortical sites, norepinephrine from hippocampal, thalamic and frontal cortical sites and acetylcholine from various cortical and subcortical sites (Menzaghi F, Sacaan A I, Reid R T, Santori E M, Correa L D, Adams P, Whelan K T, Risbrough V B, Rao T S, Schneider J S, Lloyd G K, Characterization of SIB-1508Y, the active enantiomer of a novel nicotinic acetylcholine receptor (NACHR) agonist, SIB-1765F. *Soc Neurosci Abstr* 22: 1523, 1996; Sacaan A I, Santori E M, Keegan M, Lloyd G K and Rao T S. Dopamine (DA) and norepinephrine (NE) release in the prefrontal cortex (PFC) are regulated by different nAChR subtypes. *Soc Neurosci Abstr* 23: 1200, 1997).

The effects of D-cycloserine on cognition in chronic MPTP-treated monkeys may also be due to stimulation of neurotransmitter release and enhanced function in a variety of inter-related cortical and subcortical systems. D-cycloserine may act in part to increase cortical and striatal dopamine activity since activation of NMDA receptors releases dopamine and increases dopamine neuronal firing, particularly in prefrontal cortex (Kalivas et al., 1989; Ransom R W, Deschenes N L. glycine modulation of NMDA-evoked release of [3H]acetylcholine and [3H]dopamine from rat striatal slices. *Neurosci Lett* 96:323–328, 1989). Previous studies have also shown NMDA-induced release of ACh in striatum (Ransom and Deschenes, 1989) and medial septum (Nishimura L M, Boegman R J. N-methyl-D-aspartate-evoked release of acetylcholine form the medial septum/diagonal band of rat brain. *Neurosci Lett* 115: 259–264, 1990) and cholinergic-glutamatergic interactions in cognitive function. (Aigner T G. Pharmacology of memory: cholinergic-glutamatergic interactions. *Curr Opin Neurobiol* 5:155–160, 1995; Matsuoka and Aigner, 1996b). Thus, as observed with nAChR agonists, effects of D-cycloserine on cognitive dysfunction in chronic MPTP-treated monkeys may be related to release of various neurotransmitters at several cortical and subcortical sites, as well as non-specific effects of directly enhancing glutamatergic neurotransmission.

At relatively low doses, D-cycloserine can be expected to act as a glycine agonist but at high doses, can be expected to act as a glycine antagonist. This may explain why in a previous study (Rupniak et al., 1992) D-cycloserine (used at doses of 3–14 mg/kg) failed to reverse scopolamine or phencyclidine-induced deficits in spatial delayed response performance. This may also explain the deficits induced in VD performance in our monkeys with high doses of D-cycloserine (8,000 µg/kg) but not with low doses (10, 32 or 100 µg/kg). Similar deficits in VD performance were caused by the NMDA receptor antagonist MK-801 (10–32 µg/kg). Both MK-801 and the glycine site antagonist HA-966 have previously been shown to disrupt visual recognition memory in monkeys. (Matsuoka N, Aigner T G. Cholinergic-glutamatergic interactions in visual recognition memory of rhesus monkeys. *NeuroReport* 7:565–568, 1996c). The present findings demonstrate the importance of glutamatergic neurotransmission for successful performance of our VD task, a task not affected by the primarily catecholaminergic lesion produced by chronic MPTP exposure.

In conclusion, the present findings demonstrate that a partial agonist at the glycine modulatory site of the NMDA receptor complex improves cognitive functioning in an early Parkinson model in non-human primates and may improve at least some of the cognitive deficits associated with human Parkinson's disease. Such partial agonists could also be used in combination with existing anti-Parkinsonian drugs to treat cognitive and motor dysfunction in a mammal with Parkinson's disease. Additionally, such partial agonists could also be used to work upon the glycine modulatory site of the NMDA receptor complex and improve cognitive function in subjects with schizophrenia.

I claim:

1. A method of treating cognitive dysfunction in mammals having Parkinson's disease, comprising administering a therapeutically effective amount of a partial glycine agonist to the glycine modulatory site of the NMDA receptor complex of said mammals, wherein said cognitive dysfunction is inattention.

2. The method of claim 1, wherein said partial glycine agonist is D-cycloserine, D-serine, or serine racemase.

3. A method of treating cognitive dysfunction and motor dysfunction in mammals having Parkinson's disease, comprising administering a therapeutically effective amount of a partial glycine agonist to the glycine modulatory site of the NMDA receptor complex of said mammals in combination with at least one of levodopa/carbidopa and/or a dopamine agonist, wherein said cognitive dysfunction is inattention.

4. The method of claim 3, wherein said partial glycine agonist is D-Cycloserine, D-serine or serine racemase.

5. A method of enhancing attention in a mammal comprising administering a partial glycine agonist to the glycine modulatory site of the NMDA receptor complex of said mammal.

6. The method of claim 5 wherein said patrial glycine agonist is D-cycloserine, D-serine, or serine racemase.

7. The method of claim 5 wherein said partial glycine agonist is D-serine or serine racemase.

* * * * *

UNITED STATES PATENT AND TRADEMARK OFFICE
CERTIFICATE OF CORRECTION

| | | |
|---|---|---|
| PATENT NO. | : 6,551,993 B1 | Page 1 of 1 |
| APPLICATION NO. | : 09/639611 | |
| DATED | : April 22, 2003 | |
| INVENTOR(S) | : Jay S. Schneider | |

It is certified that error appears in the above-identified patent and that said Letters Patent is hereby corrected as shown below:

In the Specification

On Column 1, Lines 9-13, please replace the existing section with the following:
-- ACKNOWLEDGEMENT OF GOVERNMENT RIGHTS This invention was made with government support under MH046531 awarded by the National Institutes of Health. The government has certain rights in the invention. --

Signed and Sealed this
Fourth Day of March, 2025

Coke Morgan Stewart
*Acting Director of the United States Patent and Trademark Office*